(12) United States Patent
Beyar et al.

(10) Patent No.: US 8,257,302 B2
(45) Date of Patent: Sep. 4, 2012

(54) USER INTERFACE FOR REMOTE CONTROL CATHETERIZATION

(75) Inventors: Rafael Beyar, Haifa (IL); Doron Linder, Haifa (IL); Eyal Zilberberg, NA Beit Halevi (IL); Tal Wenderow, Haifa (IL)

(73) Assignee: Corindus, Inc., Natick, MA (US)

( * ) Notice: Subject to any disclaimer, the term of this patent is extended or adjusted under 35 U.S.C. 154(b) by 751 days.

(21) Appl. No.: 11/920,209

(22) PCT Filed: May 10, 2005

(86) PCT No.: PCT/IL2005/000496
§ 371 (c)(1),
(2), (4) Date: Mar. 16, 2009

(87) PCT Pub. No.: WO2006/120666
PCT Pub. Date: Nov. 16, 2006

(65) Prior Publication Data
US 2009/0221958 A1  Sep. 3, 2009

(51) Int. Cl.
*A61M 31/00* (2006.01)
*A61B 1/00* (2006.01)
(52) U.S. Cl. .................................. 604/95.01; 600/106
(58) Field of Classification Search .............. 604/95.01; 600/106, 114, 117, 137, 144–146, 152; 606/1; 434/262
See application file for complete search history.

(56) References Cited

U.S. PATENT DOCUMENTS

| | | |
|---|---|---|
| 2,718,598 A | 9/1955 | Graf |
| 3,147,953 A | 9/1964 | Arth |
| 3,308,297 A | 3/1967 | Mansker |
| 4,254,341 A | 3/1981 | Herr et al. |
| 4,382,184 A | 5/1983 | Wernikoff |

(Continued)

FOREIGN PATENT DOCUMENTS

EP  0 329 492 A2  8/1989
(Continued)

OTHER PUBLICATIONS

Anderson, James, Ph.D., et al, "Virtual Reality Training in Interventional Radiology: The Johns Hopkins and Kent Ridge Digital Laboratory Experience," Interventional Radiology Education, *Seminars in Interventional Radiology*, 2002, vol. 19, No. 2, pp. 179 and 181 (2 pages), Thieme Medical Publishers, Inc., New York, NY.

(Continued)

*Primary Examiner* — Victoria P Shumate
(74) *Attorney, Agent, or Firm* — Rathe Lindenbaum LLP

(57) ABSTRACT

A remote control catheterization system comprising: a propelling device, which controllably inserts a flexible, elongate probe into the body of a patient; and a control unit, in communication with the propelling device, and comprising user controls which are operated by a user of the system remote from the patient to control insertion of the probe into the body by the propelling device, wherein the user controls include an intuitive user interface comprising a handle that can be moved longitudinally, forward and back along a longitudinal axis, and also can be moved rotationally, in rotation around the longitudinal axis; the intuitive user interface comprising motion sensors that detect longitudinal motion and rotational motion of the handle and convert them to signals; and signal communication circuitry that communicates the signals to the control unit for commanding the propelling device to move the probe in respective direction and distance as the handle.

23 Claims, 4 Drawing Sheets

U.S. PATENT DOCUMENTS

| | | |
|---|---|---|
| 4,581,538 A | 4/1986 | Lenhart |
| 4,965,456 A | 10/1990 | Huettenrauch et al. |
| 4,977,588 A | 12/1990 | Van der Ende |
| 5,049,147 A | 9/1991 | Danon |
| 5,090,044 A | 2/1992 | Kobayashi |
| 5,139,473 A | 8/1992 | Bradshaw et al. |
| 5,185,778 A | 2/1993 | Magram |
| 5,377,678 A | 1/1995 | Dumoulin et al. |
| 5,425,382 A | 6/1995 | Golden et al. |
| 5,434,775 A | 7/1995 | Sims et al. |
| 5,464,023 A | 11/1995 | Viera |
| 5,487,734 A | 1/1996 | Thorne et al. |
| 5,492,131 A | 2/1996 | Galel |
| 5,578,014 A | 11/1996 | Erez et al. |
| 5,584,078 A | 12/1996 | Saboory |
| 5,623,943 A | 4/1997 | Hackett et al. |
| 5,690,645 A | 11/1997 | Van Erp |
| 5,706,827 A | 1/1998 | Ehr et al. |
| 5,821,920 A | 10/1998 | Rosenberg et al. |
| 5,842,987 A | 12/1998 | Sahadevan |
| 5,851,182 A | 12/1998 | Sahadevan |
| 5,882,333 A | 3/1999 | Schaer et al. |
| 5,957,941 A | 9/1999 | Ream |
| 5,981,964 A | 11/1999 | McAuley et al. |
| 6,004,276 A | 12/1999 | Wright et al. |
| 6,013,038 A | 1/2000 | Pflueger |
| 6,048,300 A | 4/2000 | Thornton et al. |
| 6,083,170 A | 7/2000 | Ben-Haim |
| 6,096,004 A | 8/2000 | Meglan et al. |
| 6,126,647 A | 10/2000 | Posey et al. |
| 6,171,234 B1 | 1/2001 | White et al. |
| 6,261,247 B1 | 7/2001 | Ishikawa et al. |
| 6,266,552 B1 | 7/2001 | Slettenmark |
| 6,285,898 B1 | 9/2001 | Ben-Haim |
| 6,351,513 B1 | 2/2002 | Bani-Hashemi et al. |
| 6,375,471 B1 | 4/2002 | Wendlandt et al. |
| 6,447,504 B1 | 9/2002 | Ben-Haim et al. |
| 6,499,163 B1 | 12/2002 | Stensby |
| 6,540,670 B1 * | 4/2003 | Hirata et al. ............... 600/152 |
| 6,554,472 B1 | 4/2003 | Dietz et al. |
| 6,610,007 B2 * | 8/2003 | Belson et al. ............... 600/146 |
| 6,705,990 B1 | 3/2004 | Gallant et al. |
| 6,726,675 B1 | 4/2004 | Beyar |
| 6,740,103 B2 | 5/2004 | Werp et al. |
| 6,770,066 B1 | 8/2004 | Leighton et al. |
| 6,835,173 B2 * | 12/2004 | Couvillon, Jr. ............. 600/146 |
| 6,878,106 B1 | 4/2005 | Herrmann |
| 6,997,870 B2 * | 2/2006 | Couvillon, Jr. ............. 600/146 |
| 7,087,013 B2 * | 8/2006 | Belson et al. ............... 600/145 |
| 7,112,811 B2 | 9/2006 | Lemer |
| 7,276,044 B2 | 10/2007 | Ferry et al. |
| 7,608,847 B2 | 10/2009 | Rees |
| 7,615,042 B2 | 11/2009 | Beyar et al. |
| 7,666,135 B2 * | 2/2010 | Couvillon, Jr. ............. 600/146 |
| 7,697,972 B2 | 4/2010 | Verard et al. |
| 7,706,894 B2 * | 4/2010 | Stewart et al. ............... 607/122 |
| 7,729,743 B2 * | 6/2010 | Sabczynski et al. .......... 600/424 |
| 7,769,427 B2 * | 8/2010 | Shachar ....................... 600/424 |
| D626,250 S | 10/2010 | Wenderow et al. |
| 7,811,294 B2 * | 10/2010 | Strommer et al. ............ 606/108 |
| 7,848,788 B2 * | 12/2010 | Tulley et al. ................ 600/423 |
| 7,887,549 B2 | 2/2011 | Wenderow et al. |
| 2002/0087166 A1 * | 7/2002 | Brock et al. ................ 606/130 |
| 2002/0109107 A1 | 8/2002 | Goldstein |
| 2002/0168618 A1 | 11/2002 | Anderson et al. |
| 2002/0177789 A1 | 11/2002 | Ferry et al. |
| 2003/0069719 A1 | 4/2003 | Cunningham et al. |
| 2003/0078003 A1 | 4/2003 | Hunter et al. |
| 2003/0176770 A1 | 9/2003 | Merril et al. |
| 2003/0199848 A1 | 10/2003 | Ledesma et al. |
| 2003/0210259 A1 * | 11/2003 | Liu et al. ..................... 345/702 |
| 2004/0044279 A1 | 3/2004 | Lewin et al. |
| 2004/0064086 A1 | 4/2004 | Gottlieb et al. |
| 2004/0068173 A1 | 4/2004 | Viswanathan |
| 2004/0085294 A1 * | 5/2004 | Michelitsch et al. ......... 345/156 |
| 2004/0113498 A1 | 6/2004 | Kroenke |
| 2004/0138548 A1 | 7/2004 | Strommer et al. |
| 2004/0254566 A1 | 12/2004 | Plicchi et al. |
| 2005/0222554 A1 | 10/2005 | Wallace et al. |
| 2005/0256504 A1 | 11/2005 | Long et al. |
| 2006/0041181 A1 | 2/2006 | Viswanathan et al. |
| 2006/0066574 A1 * | 3/2006 | Kim et al. ..................... 345/161 |
| 2006/0229587 A1 * | 10/2006 | Beyar et al. .................. 604/510 |
| 2007/0043338 A1 | 2/2007 | Moll et al. |
| 2007/0083193 A1 | 4/2007 | Werneth et al. |
| 2007/0103437 A1 | 5/2007 | Rosenberg |
| 2007/0142749 A1 | 6/2007 | Khatib et al. |
| 2007/0185486 A1 | 8/2007 | Hauck et al. |
| 2007/0197896 A1 | 8/2007 | Moll et al. |
| 2007/0250097 A1 | 10/2007 | Weitzner et al. |
| 2007/0276216 A1 | 11/2007 | Beyar et al. |
| 2007/0276234 A1 * | 11/2007 | Shahidi ........................ 600/437 |
| 2008/0027313 A1 | 1/2008 | Shachar |
| 2008/0059598 A1 | 3/2008 | Garibaldi et al. |
| 2008/0167750 A1 | 7/2008 | Stahler et al. |
| 2008/0217564 A1 | 9/2008 | Beyar et al. |
| 2009/0012533 A1 | 1/2009 | Barbagli et al. |
| 2009/0105639 A1 | 4/2009 | Weitzner et al. |
| 2009/0110152 A1 | 4/2009 | Manzke et al. |
| 2009/0131955 A1 | 5/2009 | Wenderow et al. |
| 2009/0137952 A1 | 5/2009 | Ramamurthy et al. |
| 2009/0138025 A1 | 5/2009 | Stahler et al. |
| 2009/0221958 A1 | 9/2009 | Beyar et al. |
| 2009/0247944 A1 | 10/2009 | Kirschenman et al. |
| 2010/0069833 A1 | 3/2010 | Wenderow et al. |
| 2010/0076308 A1 | 3/2010 | Wenderow et al. |
| 2010/0076309 A1 | 3/2010 | Wenderow et al. |
| 2010/0076310 A1 | 3/2010 | Wenderow et al. |
| 2011/0144658 A1 | 6/2011 | Wenderow et al. |
| 2011/0152882 A1 | 6/2011 | Wenderow et al. |

FOREIGN PATENT DOCUMENTS

| | | |
|---|---|---|
| EP | 0 331 944 A1 | 9/1989 |
| EP | 0 554 986 B1 | 8/1993 |
| EP | 0 590 268 B1 | 4/1994 |
| EP | 0 970 663 A1 | 1/2000 |
| EP | 1 415 660 A1 | 5/2004 |
| EP | 1 442 720 A1 | 8/2004 |
| EP | 1 504 713 B1 | 2/2005 |
| WO | WO 01/74252 A2 | 10/2001 |
| WO | WO 02/09571 A2 | 2/2002 |
| WO | WO 2006/120666 A1 | 11/2006 |
| WO | WO 2009/137410 A1 | 11/2009 |
| WO | WO 2010/025336 A1 | 3/2010 |
| WO | WO 2010/025338 A1 | 3/2010 |
| WO | WO 2010/068783 A1 | 6/2010 |
| WO | WO 2010/107916 A1 | 9/2010 |
| WO | WO 2011/046874 A1 | 4/2011 |

OTHER PUBLICATIONS

U.S. Appl. No. 29/378,948, filed Nov. 11, 2010, Murphy.

Beyar et al., "Remote-Control Percutaneous Coronary Interventions: Concept, Validation, and First-in-Humans Pilot Clinical Trial," Journal of the American College of Cardiology, Jan. 17, 2006, 5 pages.

International Search Report for International Application No. PCT/IL2005/000496; date of mailing Dec. 29, 2005; (2 pages).

* cited by examiner

USER INTERFACE FOR REMOTE CONTROL CATHETERIZATION

FIELD OF THE INVENTION

The present invention relates generally to invasive medical probes and methods, and specifically to intravascular catheterization and catheterization techniques.

BACKGROUND OF THE INVENTION

Catheters are used for many medical procedures, including inserting a guide wire, delivering a stent, and delivering and inflating a balloon.

Catheterization procedures are very commonly performed for diagnosis and treatment of diseases of the heart and vascular system. The catheterization procedure is generally initiated by inserting a guide wire into a blood vessel in the patient's body. The guide wire is then guided to the desired location, most commonly in one of the heart vessels or elsewhere in the vascular system. At this point the catheter is slid over the guide wire into the blood vessel and/or heart. Once the catheter is in the desired position, the guide wire can then be removed, leaving the catheter in location. Alternatively, in some procedures, the catheter is inserted without using a guide wire. The catheter may be used to pass ancillary devices into the body, such as an angioplasty balloon, or to perform other diagnostic or therapeutic procedures.

In order to facilitate the guide wire insertion and the subsequent catheter application, the physician generally performs the procedure with the assistance of a fluoroscope, as is well known in the art. The fluoroscope produces a real-time image showing the continued progress of the guide wire, or the catheter, through the patient's body.

The fluoroscope generates a high level of X-ray radiation, which poses a significant danger to medical personnel exposed thereto, as is well known in the art. In order to provide protection from radiation exposure, the attending medical personnel generally wear a heavy, cumbersome protective lead garment which covers the entire body and neck, or use various lead shields including transparent glass face and eye shields.

It is desirable to know the precise linear and rotational state of the catheter. Japanese patent no. 2000-010467 (2000) by Tokai Rika Co Ltd. et al, "CATHETER OPERATION SIMULATOR AND SIMULATION METHOD USING THE SAME" mentions a catheter operation simulator characterized by having an insertion/rotation detection sensor which outputs detected insertion/rotation data, providing the amount of insertion and rotation of a catheter tube. However the Tokai Rika patent is focused on simulation and provides only position feedback—not active means for controlling position.

One way to improve control of the catheter is to provide a control system that moves the catheter via motors. One such system is described in PCT publication no. WO/99/45994 (1999), by Dalia Beyar "REMOTE CONTROL CATHETERIZATION", which describes a remote control catheterization system including a propelling device, which controllably inserts a flexible, elongate probe into the body of a patient. A control console, in communication with the propelling device, includes user controls which are operated by a user of the system remote from the patient to control insertion of the probe into the body by the propelling device.

It is an object of some aspects of the WO/99145994 invention to provide apparatus and methods of catheterization that allow medical personnel to be distanced from the vicinity of the fluoroscope and its resultant radiation, thereby reducing radiation exposure of the personnel. It is a further object of some aspects of the WO/99145994 invention to provide a mechanism for remote control performance of catheterization procedures.

The present invention is intended to provide an intuitive user interface to a remote control catheterization system, such as WO99/45994. The present invention is based on a handle element that provides the user with an experience that closely resembles actual insertion and rotation of a catheter or guide wire. More specifically, the present invention enables the user to move the handle along a longitudinal axis and around that axis, thereby emulating the primary types of motion associated with insertion of a catheter or guide wire (herein "catheter" applies equally for a catheter or a guide wire).

In a preferred embodiment of the present invention, the user's movement of the handle is translated by the system to movement of the catheter.

In a preferred embodiment of the present invention, feedback from the catheter is converted by the invention to tactile forces acting on the handle.

In a preferred embodiment of the present invention, the translation (handle to catheter) ratio and the tactile feedback (catheter to handle) ratio are user-controlled.

In a preferred embodiment of the present invention, indicators and controls, are included on the base of the handle or in proximity.

In a preferred embodiment of the present invention, a safety mechanism is provided to ensure that the handle does not move the catheter accidentally.

In summary, it is a main object of the present invention to provide a user interface for remote control catheterization with the following several objects and advantages:
  easy to grasp
  provides operator with safe, intuitive, precise control of linear and rotational movement of the catheter
  provides the operator with tactile feedback regarding forces acting on the catheter
  provides operator with means for varying the scaling of the control signals sent and feedback received
  provides operator with easy access to controls for catheter operations, such as injecting a contrasting agent or inflating a balloon.

Still further objects and advantages will become apparent from a consideration of the ensuing description and drawings.

BRIEF DESCRIPTION OF THE INVENTION

There is thus provided, in accordance with some preferred embodiments of the present invention, a remote control catheterization system comprising: a propelling device, which controllably inserts a flexible, elongate probe into the body of a patient; and a control unit, in communication with the propelling device, and comprising user controls which are operated by a user of the system remote from the patient to control insertion of the probe into the body by the propelling device, wherein
  the user controls include an intuitive user interface comprising a handle that can be moved longitudinally, forward and back along a longitudinal axis, and also can be moved rotationally, in rotation around the longitudinal axis;
  the intuitive user interface comprising motion sensors that detect longitudinal motion and rotational motion of the handle and convert them to signals; and signal communication circuitry that communicates the signals to the control unit for commanding the propelling device to move the probe in respective direction and distance as the handle.

Furthermore, in accordance with some preferred embodiments of the present invention, the intuitive user interface is further provided with positioners that move the handle longitudinally, forward and back along its longitudinal axis, and move it rotationally, in rotation around its longitudinal axis, and wherein:

the remote control catheterization system includes at least one sensor that detects forces acting longitudinally or rotationally upon the probe and communicates this feedback information to the control console;

the control console is adapted to convert the feedback to commands for the positioners and send the commands to the signal communication circuits; and the signal communication circuits are adapted to receive the commands from the processing device and send them to the positioners, which apply longitudinal or rotational forces upon the handle that replicate the longitudinal or rotational forces experienced by the probe.

Furthermore, in accordance with some preferred embodiments of the present invention, the intuitive user interface is further provided with a fail-safe mechanism that, when activated, allows communication between the intuitive user interface and the control console and that, when deactivated, prevents the communication.

Furthermore, in accordance with some preferred embodiments of the present invention, the fail-safe mechanism is implemented as a switch that is activated when the handle is lifted up.

Furthermore, in accordance with some preferred embodiments of the present invention, the fail-safe mechanism is implemented as two contacts in the handle that are activated when brought into contact.

Furthermore, in accordance with some preferred embodiments of the present invention, the system is further equipped with a return mechanism that, upon operator release of the handle, returns the handle to an initial longitudinal and rotational position.

Furthermore, in accordance with some preferred embodiments of the present invention, the return mechanism is engaged by operator-controlled switching.

Furthermore, in accordance with some preferred embodiments of the present invention, the intuitive user interface is further equipped with a support base.

Furthermore, in accordance with some preferred embodiments of the present invention, the intuitive user interface is further equipped with operator-controlled amplification circuitry that can adjust the ratio of handle movement command sent to the probe and the force feedback from the probe to the handle.

Furthermore, in accordance with some preferred embodiments of the present invention, the intuitive user interface is further equipped with operator-controlled switches that move the handle in precise, operator-defined steps.

Furthermore, in accordance with some preferred embodiments of the present invention, the intuitive user interface is further equipped with operator-controlled switches for controlling the handle's stiffness.

Furthermore, in accordance with some preferred embodiments of the present invention, the intuitive user interface is further equipped with operator-controlled switches for controlling the ratio of handle speed to catheter speed.

Furthermore, in accordance with some preferred embodiments of the present invention, the intuitive user interface is further equipped with operator-controlled switches that send control signals via the signal communication circuits to command probe operations, including:

inflating a balloon;
injecting contrast agent.
deploying a stent

BRIEF DESCRIPTION OF THE FIGURES

The invention is described herein, by way of example only, with reference to the accompanying Figures, in which like components are designated by like reference numerals.

DETAILED DESCRIPTION OF THE INVENTION

The present invention discloses a remote control catheterization system and method employing an intuitive user interface. Such a system controllably inserts an elongate probe, typically a catheter, into a patient's body. For the purpose of the present invention "catheter" and "probe" are used to refer to any type of device that is inserted in a patient's body in a catheterization process.

The present invention provides a remote control catheterization system or method, such as that of PCT publication no. WO/99/45994 (1999), by Dalia Beyar "REMOTE CONTROL CATHETERIZATION", which is included herein by reference. The innovation of the present invention is the user interface that it provides. While the user interface of the present invention is particularly suited for integration with WO/99/45994, it can generally be used with any remote control catheterization system or method.

Figure 1:
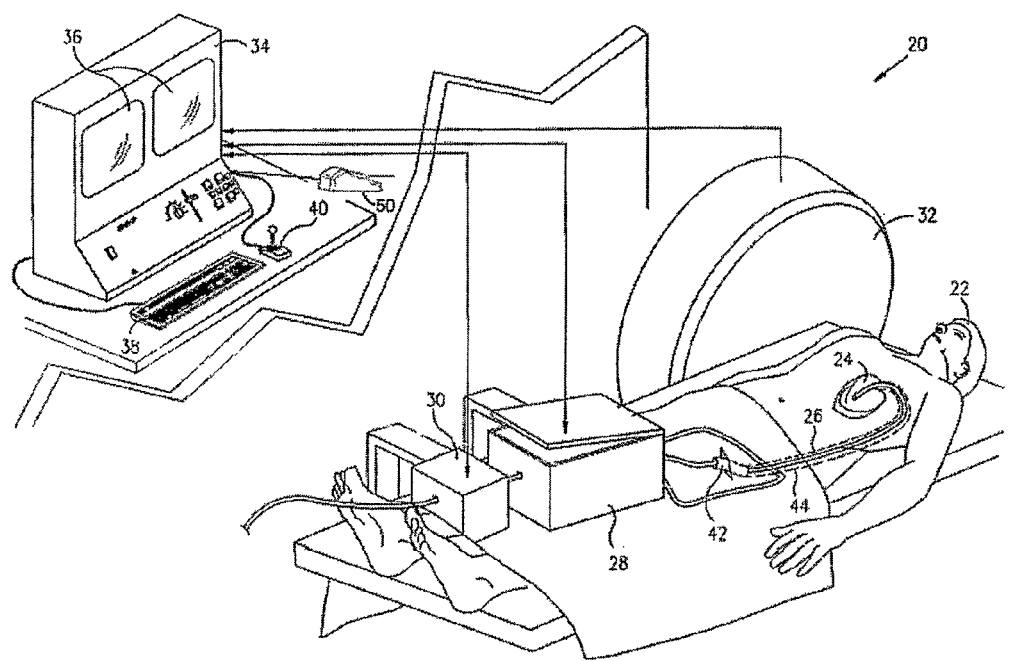
FIG. 1 is a view of the intuitive user interface of a remote control catheterization system, in accordance with a preferred embodiment of the present invention.

Reference is now made to FIG. 1, which is a simplified, pictorial illustration of a remote control catheterization system 20, in accordance with a preferred embodiment of the present invention. The invention of WO/99/45994 is summarized as follows:

System 20 comprises a guiding catheter 26, which is fed via a cannula 42 into a blood vessel 44 leading to a target location in a vessel or a heart 24 of a patient 22.

Preferably, the catheter is fed over a guide wire, which is omitted in FIG. 1 for simplicity.

Catheter 26 is fed through a catheter propelling device 28, and then coupled proximally with a catheter interface 30.

Interface 30 may be used to perform various therapeutic and/or diagnostic catheter procedures, such as balloon inflation or injection of contrast media, or any other such catheter-based treatments known in the art. A fluoroscope 32 is used to capture images showing the position of catheter 26 in the patient's body. (For simplicity, the X-ray tube associated with the fluoroscope is not shown in the figure.) Propelling device 28, interface 30 and fluoroscope 32 all communicate with a control console 34. The various elements of system 20 relay operative information to console 34, and receive operative instructions from the console. Preferably, device 28 relays to console 34 force measurements associated with insertion of the catheter and an indication of the distance that the catheter has traveled; interface 30 relays applicable data from the catheter regarding the therapeutic and/or diagnostic procedures being performed; and fluoroscope 32 conveys X-ray images.

The data are preferably displayed on console 34 via a pair of displays, monitors 36. Preferably, one of monitors 36 displays fluoroscopic images, and the other monitor displays data [RECEIVED] from propelling device 28 and interface 30.

Alternatively, the data may be presented using dials, meters, or any means known and used in the art.

Console 34 also includes a user-interface peripheral device 38 and a speed-direction interface device (which replaces all or part of tactile control unit 40 of WO/99145994). Medical personnel operating system 20 use device 38, preferably a keyboard, to send directional commands, for example to control table and fluoroscope motions, and to operate interface 30 and fluoroscope 32. intuitive user interface device 50, preferably a handle with tactile and speed feedback, sends directional and speed instructions to propelling device 28. Optionally, it can include all or some of the controls that are otherwise implemented in peripheral device 38.

In order to prevent exposure by medical staff to the fluoroscope's high levels of radiation, console 34 is preferably located outside of the catheterization room or in an area of the room that is shielded from radiation generated by the fluoroscope X-ray tube. The present invention, via this usage of remote control communication with console 34, thus furnishes the medical staff with all the relevant information, and all the relevant remote control means, to perform the catheterization operation without danger of radiation exposure.

Alternatively or additionally, console 34, or certain elements thereof, may be in a remote location, even in a different city from the patient, and communicate with the other elements of system 20 over telecommunication channels. As noted above with reference to FIG. 1, cannula 42 is inserted into blood vessel 44. Preferably a guide wire (not shown) is threaded through cannula 42 into vessel 44. Once the guide wire is in a desired position, catheter 26 is slipped over guide wire 46 and guided to a desired position, for example, in one of the chambers of heart 24 or in one of the coronary arteries.

Once catheter 26 is in place, guide wire 46 may be withdrawn if desired. An ancillary instrument (not shown), such as an angioplasty balloon, may be passed through the catheter, into the heart or arteries. The guide wire, catheter and ancillary instrument are themselves substantially similar to devices of these types known in the art.

The intuitive user interface device 50 of the present invention electronically communicates with the control console 34. A primary use of device 50 is to convert an operator's movements into signals to the control console 34 from whence they are translated into control signals to catheter propelling device 28, thereby controlling movement of the catheter 26 inside patient 22.

If the catheter is equipped with sensors that detect forces on the catheter, these can be relayed by the control console 34 to the device of the present invention 50, which can be further equipped to translate those signals into calibrated forces on the device, thereby transmitting to the device operator a tactile sense of what is happening to the catheter.

The device can be further equipped with controls enabling the operator to activate various catheter functions, such as balloon inflation, guide wire delivery, or stent insertion.

Figure 2:
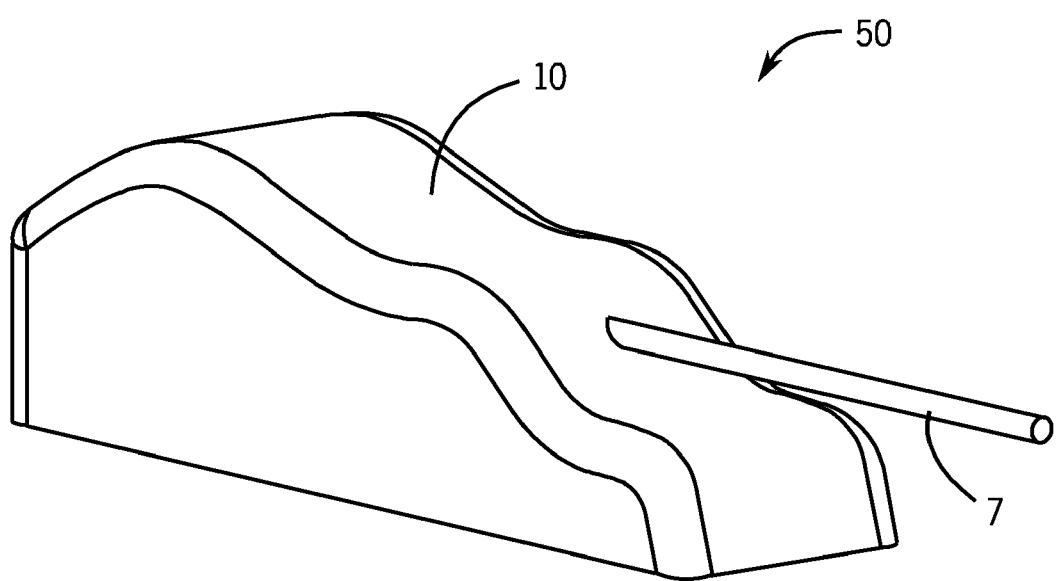
FIG. 2 is an external view of the intuitive user interface of a remote control catheterization system, in accordance with a preferred embodiment of the present invention.
Figure 3:
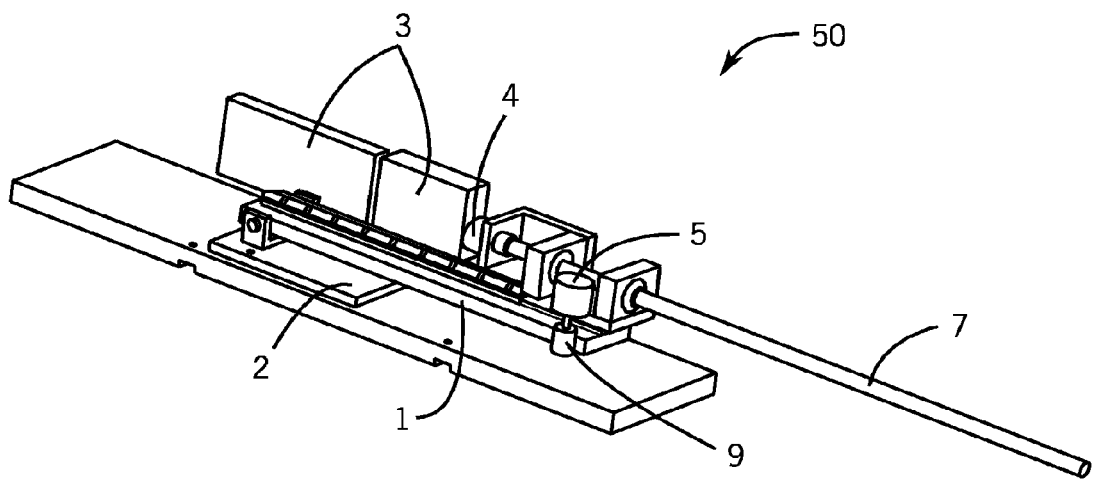
FIG. 3 is a view of the primary components of the intuitive user interface of a remote control catheterization system, in accordance with a preferred embodiment of the present invention.

The components of intuitive user interface device 50 are now described with reference to FIG. 2 (external view) and FIG. 3 (internal view).

The primary component of device 50 is an element that is capable of translating to the catheter an operator's linear movement along its longitudinal axis as well an operator's rotational movement around about that axis. In a preferred embodiment, this element is a handle 7, and the operator is a human operator 25, such as a skilled physician. However, operation of the device could equally be incorporated into an automated system.

Handle 7 is grasped by operator 25 at one end, herein the proximal end. The distal end of handle 7 engages other device components that translate handle 7 motion effected by the operator 25 to predetermined movement of catheter 26 (which comprises catheter and system that moves catheter). In a preferred embodiment of this invention, this translation is implemented as follows:

linear movement towards the handle's distal end causes the catheter to be proportionally inserted further into the patient;

linear movement away from the handle's distal end causes the catheter to be proportionally retracted from the patient;

rotational movement in either direction causes the catheter to be proportionally moved in the same rotational direction.

The two types of movement can be effected simultaneously. For example, the operator can turn the handle while at the same time inserting it, and both these motions will translated simultaneously to the catheter.

The proportion of handle distance moved to catheter distance moved is operator-controlled.

Intuitive user interface 50 sends data to control console 34 concerning movement of handle 7. Control console 34 generates drive signals to catheter interface 30 and receives tactile feedback back from interface 30. Interface circuits between control console 34 and Intuitive user interface 50 device's several sensors and motors are represented in FIG. 3 as circuit board 3.

Handle 7 can include a fail-safe release that provides a measure of safety by disengaging the system from the handle when not in use. In other words, when the safety is engaged, movement of the handle is not translated to the catheter. This prevents inadvertent or unintended movement of the catheter. In a preferred embodiment of the present invention, the fail-safe release is implemented as a metal fail-safe contact 1 physically connected to handle 7. When handle 7 is not in use, contact 1 lies in contact with fail-safe sensor 2, thereby closing the fail-safe circuit, which disengages the handle from the system. When operator 25 operates the handle, he (he refers herein to he or she) lifts up the handle, thereby breaking the fail-safe circuit and reengaging the system. A secondary aspect of reengaging the system is for control console 34 to start measuring handle movement (via feedback from transducers 4 and 5 as described later).

In an alternative preferred embodiment of the present invention, the fail-safe activation circuit can be implemented as one of controls 15.

In another alternative embodiment of the present invention, handle 7 can be implemented as two strips that also perform the fail-safe function. When operator 25 squeezes the handle, bringing the strips into contact, it activates a circuit that engages the system.

Rotational movement of handle 7 is detected by rotation transducer 4 (which can be a potentiometer, encoder, or other device measuring movement and translating the movement into an electrical signal), which sends a corresponding signal via circuits 3 to control console 34.

Linear movement of handle 7 turns linear movement detector wheel 9, which in turn moves linear transducer 5 (which can be a potentiometer, encoder, or other device measuring movement and translating the value into an electrical signal), which sends a corresponding signal via circuits 3 to control console 34.

In a preferred embodiment of the present device, catheter propelling device 28 is equipped to detect forces acting on the distal end of the catheter 26 (inside the patient) during the catheterization procedure. Feedback motors (or other positioner device) 21 and 22, on the handle's 7 linear and rotational axes of movement, provide feedback to the operator 25, transferring forces detected on the catheter to the handle. The feedback motor mechanism can be activated/deactivated by operator 25, through controls 15 or similar means.

Feedback motors 21 and 22 enable the operator 25 to feel what is happening to the catheter as he or she navigates it. The feedback force translation can be a ratio of 1:1 or scaled. For example, if the operator 25 wants to more easily detect small forces acting on the catheter, the motors can multiply the force translated to the handle.

In addition to providing feedback about the catheter, motors 21 and 22 can be calibrated by the operator 25 to determine the handle's 7 level of stiffness along each axis of movement (linear and rotational). For example, the stiffness can be calibrated to increase proportionally to the amount of opposing force experienced by the catheter.

Handle 7 is optionally further equipped with return components which return the handle to its original position when the operator 25 releases the handle. The return can be effected with dedicated components, such as motors or springs, or integrated into the feedback motors and their control circuit. In a preferred embodiment, return component is implemented as springs 13 and 14. Return of the handle to its original position does not have to be coupled to the catheter, in other words, the catheter is not moved when the handle returns to its zero. However, this type of linkage can be left to operator discretion, as expressed via controls 15 or similar means.

Handle 7 is further equipped with handle controls 15 for operator 25 interaction with control console 34 and catheter 26. Controls can include:

Engaging handle—acting as a safety switch that must be activated for the handle to affect the catheter Controlling linkage of handle and catheter, for example, determining that catheter is not affected when return mechanism returns handle to zero.

Determining the amount of force feedback for each type of movement (linear and rotational)

Determining the amount of stiffness

Determining the ratio of catheter movement to handle movement. For example, the operator 25 could choose a 1:10 ratio in which case a 1 cm handle movement would move the catheter 1 mm.

Determining the ratio of catheter speed to handle speed. For example, the operator 25 could choose a 10:1 ratio, in which case 1 cm/s of handle speed is translated into 1 mm of catheter speed.

Moving in incremental steps of operator-determined size, for example, moving the handle (and catheter) 1 cm on each activation of the control.

Activating catheter operations, for example, injecting contrast agent.

Activating a device in the catheter, for example, inserting a stent or inflating a balloon.

Inserting a guide wire.

Changing the target of the device activation function from one device to another, for example, from a guide wire to a stent.

Figure 4:
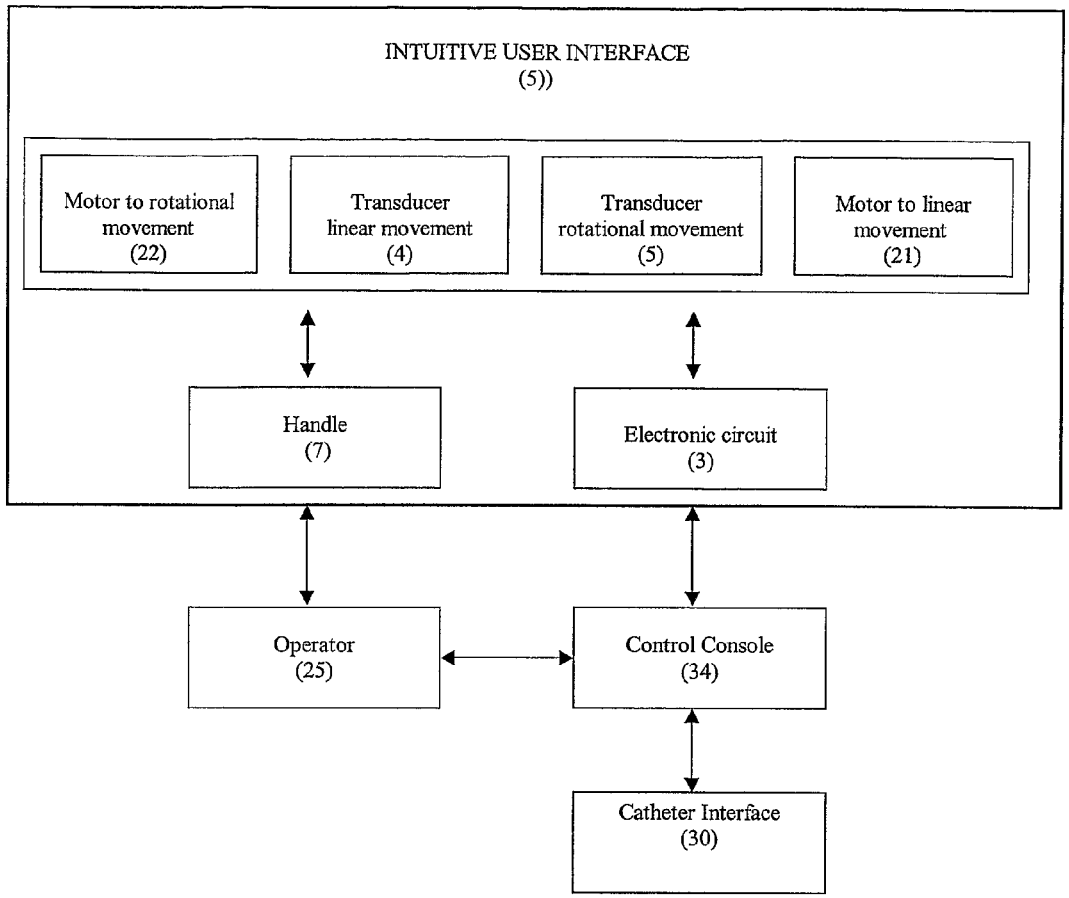
FIG. 4 is a block diagram for a method of intuitive user operation of a remote control catheterization system, in accordance with a preferred embodiment of the present invention.

Device operation is now described with reference to FIG. 4.

Operator 25 moves handle 7 in desired linear and/or rotational direction. Linear transducer 5 and rotational transducer 4 each transmit a signal via integration circuit 3 to control console 34, which translates the movement to motorized catheterization system 26. The translated movement can be scaled, according to how operator 25 sets controls 15. As catheter 26 moves, it encounters forces from obstacles and other characteristics of its path. Catheterization system 26 relays this information to control console 34, which translates the signals into control signals for linear feedback motor 21 and rotary feedback motor 22, which apply feedback force in same direction as that experienced by catheter to handle 7. Again, the feedback force can be direct or scaled, according to operator 25 preference.

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

The invention claimed is:

1. A remote control catheterization system comprising:
a propelling device, which controllably inserts a flexible, elongate probe into the body of a patient; and
a control unit, in communication with the propelling device, and comprising user controls which are operated by a user of the system remote from the patient to control insertion of the probe into the body by the propelling device,
wherein the user controls include an intuitive user interface comprising a handle that can be moved longitudinally, forward and back along a single longitudinal axis, and also can be moved rotationally, in rotation around the longitudinal axis;
the intuitive user interface comprising motion sensors that detect longitudinal motion and rotational motion of the handle and convert them to signals; and signal communication circuitry that communicates the signals to the control unit for commanding the propelling device to move the probe; in the same direction and distance as the handle,
the intuitive user interface including a fail-safe mechanism that, when activated, allows communication between the intuitive user interface and the control console and that, when deactivated, prevents the communication, and
wherein, the handle is a longitudinal member being horizontal in an operative position and being in a non-horizontal orientation in a non-operative position, the handle being operatively connected to a first contact that moves with the handle as the handle is moved from a horizontal to a non-horizontal orientation, the fail-safe mechanism including a second contact that does not move with the handle as the handle is moved from a horizontal to a non-horizontal orientation, the fail safe mechanism being implemented as two contacts in the handle that are activated when brought into contact, as the handle is moved from a horizontal to a non-horizontal position.

2. The system of claim 1 wherein the intuitive user interface is further provided with positioners that move the handle longitudinally, forward and back along its longitudinal axis, and move it rotationally, in rotation around its longitudinal axis, and wherein:
- the remote control catheterization system includes at least one sensor that detects forces acting longitudinally or rotationally upon the probe and communicates this feedback information to a control console;
- the control console is adapted to convert the feedback to commands for the positioners and send the commands to the signal communication circuits; and
- the signal communication circuits are adapted to receive the commands from the processing device and send them to the positioners, which apply longitudinal or rotational forces upon the handle that replicate the longitudinal or rotational forces experienced by the probe.

3. The system of claim 2 wherein the intuitive user interface is further equipped with operator-controlled amplification circuitry that can adjust the ratio of handle movement command sent to the probe and the force feedback from the probe to the handle.

4. The system of claim 1 wherein the fail-safe mechanism is implemented as a switch that is activated when the handle is lifted up.

5. The system of claim 1 wherein the intuitive user interface is further equipped with a support base, the second contact being fixed relative to the support base, the handle and first contact being operatively pivoted to the base about a pivot.

6. The system of claim 1 wherein the intuitive user interface is further equipped with operator-controlled switches that move the handle in precise, operator-defined steps.

7. The system of claim 1 wherein the intuitive user interface is further equipped with operator-controlled switches for controlling the handle's stiffness.

8. The system of claim 1 wherein the intuitive user interface is further equipped with operator-controlled switches for controlling the ratio of handle speed to catheter speed.

9. The system of claim 1 wherein the intuitive user interface is further equipped with operator-controlled switches that send control signals via the signal communication circuits to command probe operations, including:
- inflating a balloon;
- injecting contrast agent; and
- deploying a stent.

10. The system of claim 1 wherein the elongated probe is a catheter.

11. The system of claim 1 wherein the elongate probe is a stent delivery device.

12. The system of claim 1 wherein the elongate probe is an angioplasty insertion and inflation device.

13. The system of claim 1 wherein the elongate probe is a guide wire insertion device and the handle is horizontal and has a cylindrical shape.

14. A remote control catheterization system comprising:
- a propelling device, which controllably inserts a flexible, elongate probe into the body of a patient; and
- a control unit, in communication with the propelling device, and comprising user controls which are operated by a user of the system remote from the patient to control insertion of the probe into the body by the propelling device
- wherein the user controls include an intuitive user interface comprising a handle that can be moved longitudinally, forward and back along a single longitudinal axis, and also can be moved rotationally, in rotation around the longitudinal axis;
- the intuitive user interface comprising motion sensors that detect longitudinal motion and rotational motion of the handle and convert them to signals; and signal communication circuitry that communicates the signals to the control unit for commanding the propelling device to move the probe; in the same direction and distance as the handle; and
- a return mechanism that, upon operator release of the handle, returns the handle to an initial longitudinal and rotational position, wherein the probe remains-fixed when the handle returns to the initial longitudinal and rotation position.

15. The system of claim 14 where the return mechanism may be selectively engaged by operator-controlled switching to determine whether the probe moves as the handle returns to its original longitudinal and rotational position.

16. A method for catheterization comprising: inserting an elongate, flexible probe into a body passage; feeding a portion of the probe outside the body into a propelling device, which advances the probe through the body passage; and controlling the propelling device to advance the probe from a location remote from the body, wherein:
- controlling the propelling device comprises operating an intuitive user interface comprising a handle that is moved longitudinally, forward and back along a single longitudinal axis, and also moved rotationally, in rotation around the longitudinal axis; and
- detecting via motion sensors longitudinal and rotational positions of the handle and converting them to position signals;
- communicating the position signals to a control console, via communication circuitry, thereby commanding the propelling device to move the probe the same direction and distance as the handle was moved; and
- returning, upon operator release of the handle, the handle to its original longitudinal and rotational position, and providing a control for a user to determine whether the probe moves as the handle returns to its original longitudinal and rotational position.

17. The method of claim 16 further comprising positioners, wherein the positioners are configured to move the handle longitudinally, forward and back along its longitudinal axis, and rotationally, in rotation around its longitudinal axis, and:
- detecting, by means of sensors, forces acted longitudinally and rotationally upon the probe and communicating this feedback information to the control console;
- converting, via the control console, the feedback to commands for the positioners and sending the commands to the signal communication circuits; and
- receiving, via the signal communication circuits, commands from a processing device and sending them to the positioners, the positioners applying longitudinal or rotational forces upon the handle that replicate the longitudinal or rotational forces experienced by the probe.

18. The method of claim 16 further comprising enabling, via activation of a fail-safe mechanism, communication between the intuitive user interface and the control console and disabling, via release of the fail-safe mechanism, that communication.

19. The method of claim 16 further comprising adjusting, via operator-controlled amplification circuits, the ratio of handle movement command sent to the probe and the force feedback from the probe to the handle.

20. The method of claim 16 further comprising moving, via operator-controlled switches, the handle in precise, operator-defined steps.

21. The method of claim 16 further comprising controlling, via operator-controlled switches, the handle's stiffness.

22. The method of claim 16 further comprising sending, via operator-controlled switches, control signals via the signal communication circuits to command probe operations, including:

inflating a balloon;
injecting contrast agent: and
inserting a stent.

23. The method of claim 16 further comprising processing both the longitudinal and rotational position signals simultaneously.

* * * * *